(12) United States Patent
Chen et al.

(10) Patent No.: US 10,211,360 B2
(45) Date of Patent: Feb. 19, 2019

(54) OPTICAL BIOSENSOR MODULE AND METHOD FOR MAKING THE SAME

(71) Applicants: LITE-ON OPTO TECHNOLOGY (CHANGZHOU) CO., LTD., Jiangsu Province (CN); LITE-ON TECHNOLOGY CORP., Taipei (TW)

(72) Inventors: Hung-Jui Chen, Taipei (TW); Tsan-Yu Ho, Taipei (TW); Meng-Sung Chou, Taipei (TW)

(73) Assignees: Lite-On Opto Technology (Changzhou) Co., Ltd., Jiangsu Province (CN); Lite-On Technology Corp., Taipei (TW)

( * ) Notice: Subject to any disclaimer, the term of this patent is extended or adjusted under 35 U.S.C. 154(b) by 0 days.

(21) Appl. No.: 15/795,739

(22) Filed: Oct. 27, 2017

(65) Prior Publication Data

US 2018/0145205 A1 May 24, 2018

(30) Foreign Application Priority Data

Nov. 18, 2016 (CN) .......................... 2016 1 1018509

(51) Int. Cl.
*H01L 31/167* (2006.01)
*A61B 5/0205* (2006.01)
(Continued)

(52) U.S. Cl.
CPC .......... *H01L 31/167* (2013.01); *A61B 5/0205* (2013.01); *A61B 5/14552* (2013.01); *A61B 5/6801* (2013.01); *G01J 1/0209* (2013.01); *G01J 1/0214* (2013.01); *G01J 1/08* (2013.01); *H01L 25/165* (2013.01); *H01L 25/167* (2013.01); *H01L 31/02005* (2013.01); *H01L 33/52* (2013.01); *H01L 33/62* (2013.01);
(Continued)

(58) Field of Classification Search
CPC ... H01L 31/167; H01L 25/165; H01L 25/167; H01L 31/02005; H01L 33/52; H01L 33/62; H01L 2933/005; H01L 2933/0066; A61B 5/0205; A61B 5/02433; A61B 5/0816; A61B 5/14552; A61B 2562/0023; A61B 5/681; G01J 1/0209; G01J 1/0214; G01J 1/08
See application file for complete search history.

(56) References Cited

U.S. PATENT DOCUMENTS

6,169,295 B1 * 1/2001 Koo ...................... H01L 31/167
257/100
2016/0206221 A1 * 7/2016 Kim .................... A61B 5/02427
(Continued)

*Primary Examiner* — Sitaramarao S Yechuri
(74) *Attorney, Agent, or Firm* — Rosenberg, Klein & Lee (57) ABSTRACT

An optical biosensor module includes a circuit board having a mounting surface and first and second circuits. A light-receiving unit is disposed on the mounting surface, and includes a light receiver electrically connected to the first circuit and having a light-receiving surface. A light-emitting unit is disposed on the light-receiving surface, and includes a light emitter electrically connected to the second circuit and having a light-emitting surface, and a light emitter blocking wall surrounding the light emitter. An opaque interface exists between the light receiver and the light emitter, and a top side of the light emitter blocking wall is equal to or higher than the light-emitting surface.

13 Claims, 9 Drawing Sheets

(51) Int. Cl.
- *A61B 5/1455* (2006.01)
- *G01J 1/02* (2006.01)
- *G01J 1/08* (2006.01)
- *H01L 25/16* (2006.01)
- *H01L 31/02* (2006.01)
- *H01L 33/52* (2010.01)
- *H01L 33/62* (2010.01)
- *A61B 5/00* (2006.01)
- *A61B 5/024* (2006.01)
- *A61B 5/08* (2006.01)

(52) U.S. Cl.
CPC ......... *A61B 5/02433* (2013.01); *A61B 5/0816* (2013.01); *A61B 2562/0238* (2013.01); *H01L 2224/05554* (2013.01); *H01L 2224/48091* (2013.01); *H01L 2224/49175* (2013.01); *H01L 2224/73265* (2013.01); *H01L 2933/005* (2013.01); *H01L 2933/0066* (2013.01)

(56) References Cited

U.S. PATENT DOCUMENTS

2016/0300988 A1* 10/2016 Oh ................... H01L 33/60
2017/0215779 A1*  8/2017 Koide ............... A61B 5/14532
2017/0354335 A1* 12/2017 Bower ............... A61B 5/02427

* cited by examiner

OPTICAL BIOSENSOR MODULE AND METHOD FOR MAKING THE SAME

CROSS REFERENCE TO RELATED APPLICATION

This application claims priority of Chinese Patent Application No. 201611018509.4, filed on Nov. 18, 2016.

FIELD

The disclosure relates to an optical biosensor module, more particularly to a wearable device including thereof and a method for making the same.

BACKGROUND

Recently, a photoplethysmography (PPG) sensor has been gradually installed in many wearable devices to detect and measure the health related information, such as cardiac rhythm, blood oxygen, etc.

Figure 1:
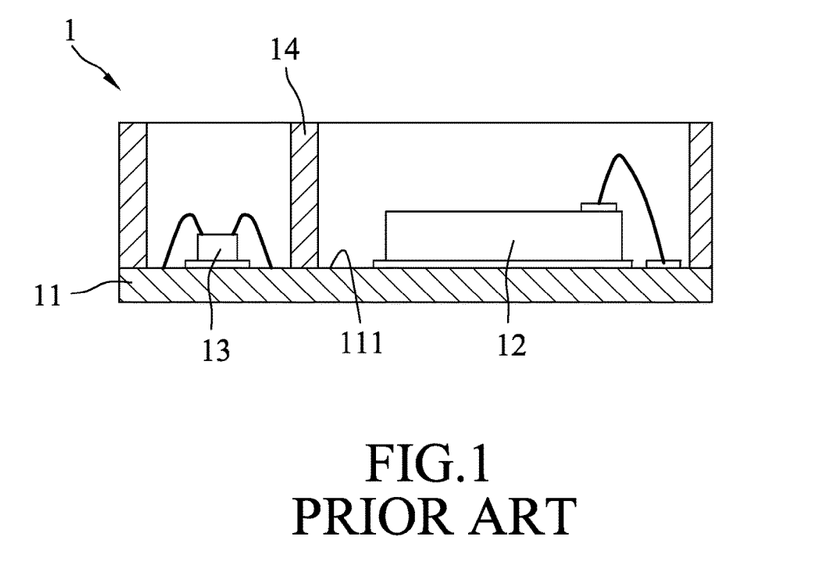
FIG. 1 is a sectional view of an existing optical biosensor module.

Referring to FIG. 1, an existing optical biosensor module 1 includes a printed circuit board (PCB) 11, a light receiver 12 and a light emitter 13 both disposed on a same plane 111 of the PCB 11, and a light blocking wall 14 formed between thereof. However, when this kind of optical biosensor module 1 is installed on a wearable device, it will be difficult to further miniaturize the wearable device.

How to improve the structure of the optical biosensor module 1 so that the size of the wearable device can be thinner is a problem to be resolved by skilled persons in this art.

SUMMARY

Therefore, an object of the present disclosure is to provide an optical biosensor module that can alleviate at least one of the drawbacks of the prior art.

According to one aspect of this disclosure, an optical biosensor module includes a circuit board, a light-receiving unit and a light-emitting unit disposed above thereof. The circuit board includes a mounting surface, a first circuit and a second circuit. The light-receiving unit is disposed on the mounting surface, and includes a light receiver electrically connected to the first circuit and having a light-receiving surface that faces away from the mounting surface. The light-emitting unit is disposed on the light-receiving surface and includes a light emitter electrically connected to the second circuit and having a light-emitting surface that faces away from the light-receiving surface, and a light emitter blocking wall surrounding the light emitter. In this disclosure, an opaque interface exists between the light receiver and the light emitter, and a top side of the light emitter blocking wall is equal to or higher than the light-emitting surface.

Another object of this disclosure is to provide a method for making an optical biosensor module.

According to another aspect of this disclosure, a method for making an optical biosensor module includes a preparation step, in which a circuit board having a mounting surface, a light receiver having a light-receiving surface, and a light emitter having a light-emitting surface are prepared; and a chip stacking step, in which the light receiver is disposed on the mounting surface, and the light emitter is disposed on a non-light transmissive layer of a die mounting region of the light-receiving surface.

The efficiency of this disclosure resides in that the light-emitting unit and the light-receiving unit are stacked one above the other on the circuit board, not only the effect of reducing the sizes of the components thereof can be achieved so that the size of the wearable device can be miniaturized, but also the light-emitting unit can be disposed close to the user so that an optical path of an incident light emitted from the light emitter to the user's skin can be shortened, thereby reducing the loss of light and achieve power saving.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Before the present disclosure is described in greater detail, it should be noted herein that like elements are denoted by the same reference numerals throughout the disclosure.

Figure 2:
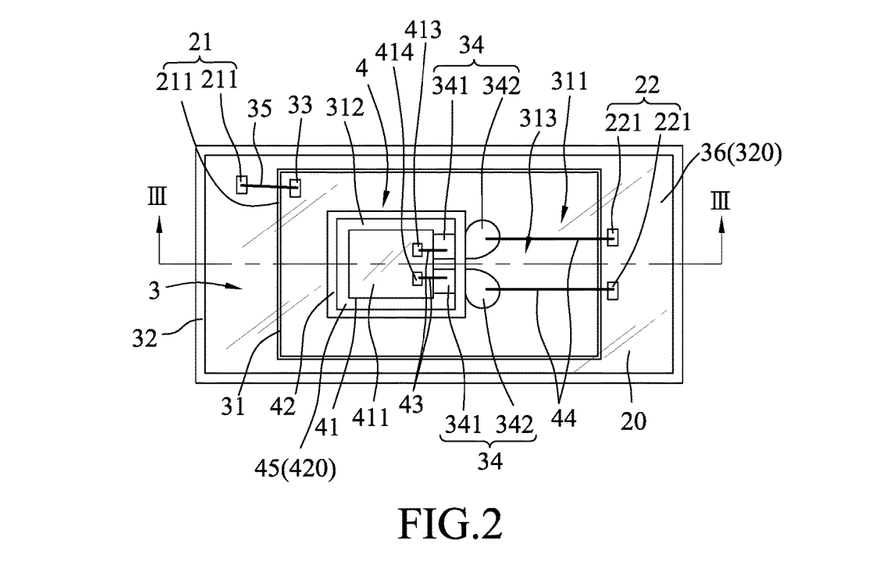
FIG. 2 is a schematic top view of an optical biosensor module according to the first embodiment of the present disclosure.
Figure 3:
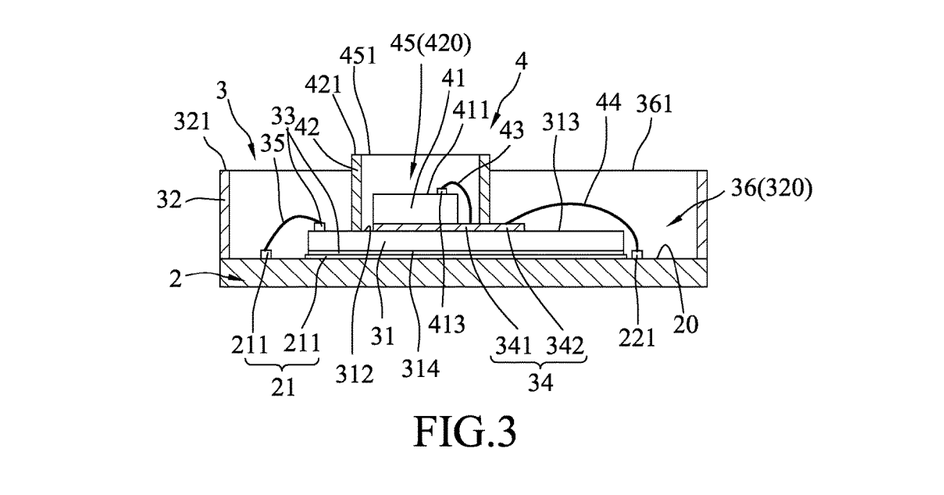
FIG. 3 is a sectional view of the first embodiment taken along line III-III of FIG. 2.

Referring to FIGS. 2 and 3, an optical biosensor module according to the first embodiment of the present disclosure is shown to include a circuit board 2, a light-receiving unit 3 and a light-emitting unit 4.

The circuit board 2 includes a mounting surface 20, and a first circuit 21 and a second circuit 22 spacedly disposed on the mounting surface 20. Wherein, each of the first circuit 21 and the second circuit 22 is formed by a conductive material, such as copper. For measuring the respiration, at least one light source is used, e.g., a light emitting diode in any suitable range of the electromagnetic spectrum, such as in the green to infrared range.

To combine measurement of the respiratory frequency with measurement of the arterial oxygen saturation ($SpO_2$) and heart function, heart beat rate, pulse, pulse oximetry is suitably employed. In pulse oximetry, at least two wavelengths must be used, typically one in the red and one in the near infrared range, such as 660 nm and 940 nm. In photoplethysmography (PPG), the wavelengths can be green, such as 570 nm.

The light-receiving unit 3 is disposed on the mounting surface 20, and includes a light receiver 31 and a light receiver blocking wall 32. The light receiver 31 refers to photodiodes. The light receiver 31 is electrically connected to the first circuit 21, and has a light-receiving surface 311 facing away from the mounting surface 20. The light-receiving surface 311 includes a die mounting region 312, and a light-receiving region 313 surrounding the die mounting region 312. In this embodiment, the light receiver 31 is a photoplethysmography (PPG) sensor, and is a vertical chip. The light receiver 31 includes a pair of first electrode pads 33 and a pair of second electrode pads 34. The light receiver blocking wall 32 is disposed on the mounting surface 20 and surrounds the light receiver 31. One of the first electrode pads 33 is disposed on the light-receiving region 313. The other first electrode pad 33 is disposed on a bottom surface 314 of the light receiver 31 which is opposite to the light-receiving surface 311, and is bonded to an electrode pad 211 of the first circuit 21 which is located below the light receiver 31. The pair of second electrode pads 34 are spacedly disposed on the light-receiving surface 311, and are spaced apart from the first electrode pads 33. Each second electrode pad 34 has an inner portion 341 located inside the die mounting region 312, and an extension portion 342 extending from the inner portion 341 to the outside of the die mounting region 312.

Specifically, in this embodiment, one way of electrical connections between the light receiver 31 and the circuit board 2 is through a conductive wire 35 of the light-receiving unit 3 interconnecting the first electrode pad 33 located on the light-receiving surface 311 and another electrode pad 211 of the first circuit 21 which is spaced apart from the light receiver 31; and the other way is through the connection of the first electrode pad 33 located on the bottom surface 314 of the light receiver 31 with the electrode pad 211 of the first circuit 21 which is located below the light receiver 21 by soldering.

The light-emitting unit 4 is disposed on the light-receiving surface 311, and includes a light emitter 41 and a light emitter blocking wall 42. The light emitter 41 is electrically connected to the second circuit 22, and has a light-emitting surface 411 facing away from the light-receiving surface 311. The light emitter 41 includes an N-type contact pad 413 and a P-type contact pad 414. Preferably, the light emitter 41 is die bonded to the die mounting region 312, and is electrically connected to the second circuit 22 through the N-type and P-type contact pads 413, 414. The light emitter blocking wall 42 is disposed on the light-receiving surface 311, and surrounds the light emitter 41 and the die mounting region 312. It should be noted herein that the light emitter 41 is mainly composed of a light emitting diode (LED) epitaxial structure, and there is no special restriction on the color and the number of the light emitter 41. The color and the number of the light emitter 41 can be adjusted according to the requirement.

The light emitter 41 of this embodiment is a horizontal chip, so that the N-type and P-type contact pads 413, 414 are disposed on the light-emitting surface 411 thereof. The light emitter 41 is die bonded to the inner portions 341 of the second electrode pads 34 using a die bonding adhesive (not shown). Through a pair of first conductive wires 43 that respectively connect the N-type and P-type contact pads 413, 414 to the inner portions 341 of the second electrode pads 34, and through a pair of second conductive wires 44 that respectively connect the extension portions 342 of the second electrode pads 34 to two electrode pads 221 of the second circuit 22, the light emitter 41 can be electrically connected to the circuit board 2. It is worth to mention herein that an opaque interface exists between the light receiver 31 and the light emitter 41, and an incident light emitted from the light emitter 41 does not penetrate from the die mounting region 312 into the light-receiving surface 311. The non-light transmissivity structure of this embodiment is mainly composed of the inner portions 341 of the second electrode pads 34. Each second electrode pad 34 may be made of a material that can prevent penetration of the incident light of the light emitter 41 therethrough, a conductive material that can reflect the incident light, such as gold or silver, or may include a die bonding adhesive that is non-light transmissive, such as silver paste.

It should be noted herein that the connection between the light emitter 41 and the light receiver 31 is not limited to the aforesaid disclosure. A distributed bragg reflector (DBR) may first be formed on the die mounting region 312 of the light receiver 31, after which the pair of the second electrode pads 34 are formed thereon, so that a side of the light emitter 41 which is opposite to the light-emitting surface 411 is die bonded to the inner portions 341 of the second electrode pads 34. The purpose of reflecting the incident light may be similarly achieved.

The connection of the light emitter 41 with the die mounting region 312 is also not limited to that described in the first embodiment. For example, (a) the light emitter 41 may be directly die-bonded to the light-receiving surface 311 through a non-light transmissive die-bonding adhesive; (b) a non-light transmissive layer (such as a black adhesive layer) is first provided on the light-receiving surface 311, after which the light emitter 41 is disposed on the non-light transmissive layer; (c) when the light emitter 41 has a horizontal structure, a metal layer with good heat dissipation may first be provided on the light-receiving surface 311, after which the light emitter 41 is disposed on the metal layer, a pair of electrode pads are disposed on the light receiver 31 spaced apart from the metal layer, and a pair of conductive wires are used to connect the light emitter 41 and the electrode pads; (d) when the light emitter 41 has a vertical structure, a pair of spaced-apart electrode pads may be directly disposed on the light receiver 31, the light emitter 41 is disposed on one of the electrode pads, and a conductive wire is used to connect the light emitter 41 with the other electrode pad; or (e) when the light emitter 41 has a flip chip structure, a pair of spaced-apart electrode pads may first be formed on the light receiver 31, after which the light emitter 41 is flipped-chip mounted to the electrode pads. Since the die-bonding manner of the light emitter 41 is well known to those skilled in the art and is not an important aspect of this disclosure, a detailed description thereof is dispensed herewith.

It is worth to mention herein that, in order to protect the light-receiving unit 3, the light-emitting unit 4, and their related electrical connections and circuits (such as the first and second electrode pads 33, 34 and the conductive wires 35, 43, 44 of this embodiment), the light-emitting unit 4 further includes a first transparent material 45, and the light-receiving unit 3 further includes a second transparent material 36. The first transparent material 45 is filled into a space 420 surrounded by the light emitter blocking wall 42 to encapsulate the light emitter 41 and cover the die mounting region 312. The second transparent material 36 is filled into a space 320 cooperatively defined by the light receiver blocking wall 32 and the light emitter blocking wall 42 to encapsulate the light receiver 31 and to cover the mounting surface 20.

When the optical biosensor module of the disclosure is disposed facing the skin of a user (not shown), the light emitter 41 can emit an incident light that penetrates the user's skin. The incident light in the skin is converted into an optical signal, and the optical signal is reflected by the skin to the light-receiving region 313 of the light-receiving surface 311, so that the light receiver 31 can receive and analyze the optical signal. In this embodiment, the light-emitting surface 411 of the light emitter 41 is lower than top sides 321, 421 of the light receiver and light emitter blocking walls 32, 42, while the top side 421 of the light emitter blocking wall 42 is equal to or higher than the top side 321 of the light receiver blocking wall 32 and is equal to or higher than the light-emitting surface 411. Further, the light receiver and light emitter blocking walls 32, 42 are respectively made of an opaque material that can block an incident light emitted from the light emitter 41 from penetrating therethrough. Preferably, a height relation of the light-emitting unit 4 relative to the light-receiving unit 3 is that a height measured from the mounting surface 20 to the top side 421 of the light emitter blocking wall 42 does not exceed twice the height of the light receiver blocking wall 32 measured from the mounting surface 20 to the top side 321 thereof. To avoid overflow of the adhesives, the height relation of the light-emitting unit 4 relative to the light-receiving unit 3 is that the height measured from the mounting surface 20 to the top side 421 of the light emitter blocking wall 42 is higher than the height of the light receiver blocking wall 32 measured from the mounting surface 20 to the top side 321 thereof by at least three percent (3%).

From the foregoing, it is evident that by allowing the light emitter blocking wall 42 to have the maximum height (that is, higher than the light receiver blocking wall 32 and the light-emitting surface 411), the incident light emitted from the light emitter 41 will not directly and laterally incident on the light-receiving surface 311 of the light receiver 31 so as to affect the light receiver 31 from receiving the optical signal. The light receiving efficiency of the light receiver 31 can thus be enhanced. It should be noted herein that the plastic material suitable for making the light receiver and light emitter blocking walls 32, 42 of the first embodiment may be sheet molding compound (SMC). For example, the sheet molding compound may be epoxy molding compound (EMC), epoxy resin, silicone, liquid crystal polymer (LCP), polyphthalamide (PPA), or polycyclohexylenedime-thylene terephthalate (PCT). Moreover, when the different aforesaid materials are used for making the light receiver and light emitter blocking walls 32, 42, the thickness range will also be different. For example, if the liquid crystal polymer (LCP) is used, the thickness thereof is preferably ≥0.2 mm; and if the epoxy resin is used, the thickness thereof is preferably ≥0.3 mm.

Since the light emitter 41 is disposed on the light receiver 31, the light emitter 41 is more proximate to the user's skin. As such, the light path of the incident light emitted from the light emitter 41 to the user's skin can be shortened, thereby reducing the loss of light. Hence, the entire optical biosensor module of this disclosure can achieve a power saving effect.

It is worth to mention herein that in order to achieve a good signal-to-noise ratio (SNR), the second transparent material 36 may include dye. Specifically, when the second transparent material 36 includes the dye, the unnecessary noise can be filtered as the optical signal travels to the light receiver 31, so that the SNR of the entire module is enhanced.

Figure 4:
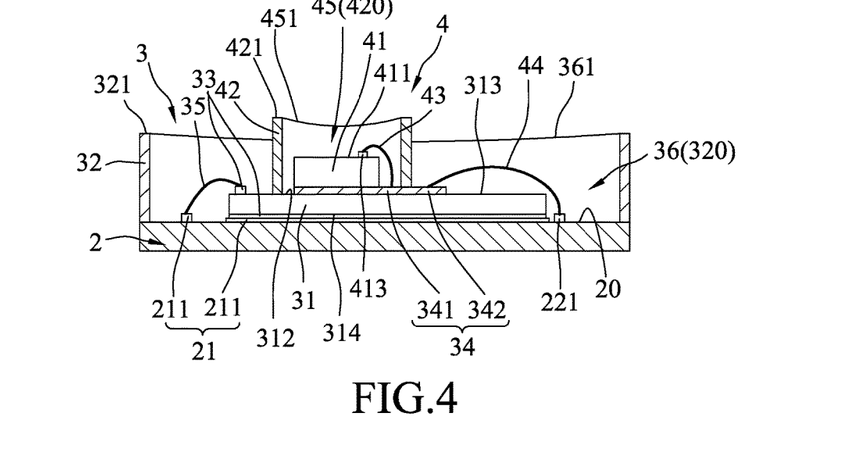
FIG. 4 is a view similar to FIG. 3, but illustrating alternative forms of a top surface of a first transparent material and a top surface of a second transparent material.

The first transparent material 45 has a top surface 451 which serves as a top surface of the light-emitting unit 4, and the second transparent material 36 also has a top surface 361 which serves as a top surface of the light-receiving unit 3. The top surface 451, 361 of each of the first and second transparent materials 45, 36 is planar, as shown in FIG. 3. Alternatively, as shown in FIG. 4, the top surface 451 of the first transparent material 45 may concave downwardly from the top side 421 of the light emitter blocking wall 42 toward the light emitter 41, and the top surface 361 of the second transparent material 36 may concave downwardly from the top side 321 of the light emitter blocking wall 32 into the space 320 defined by the light receiver and light emitter blocking walls 32, 42 toward the light receiver 31. The top surface 451 of the first transparent material 45 with the concave shape may be viewed as a concave lens for increasing the divergent angle of the incident light of the light emitter 41 leaving the first transparent material 45. The top surface 361 of the second transparent material 36 with the concave shape may be viewed as a convex lens for enhancing the light receiving effect. Moreover, the top surface 451 of the first transparent material 45 with the concave shape is higher than the top surface 361 of the second transparent material 36 with the concave shape.

Figure 5:
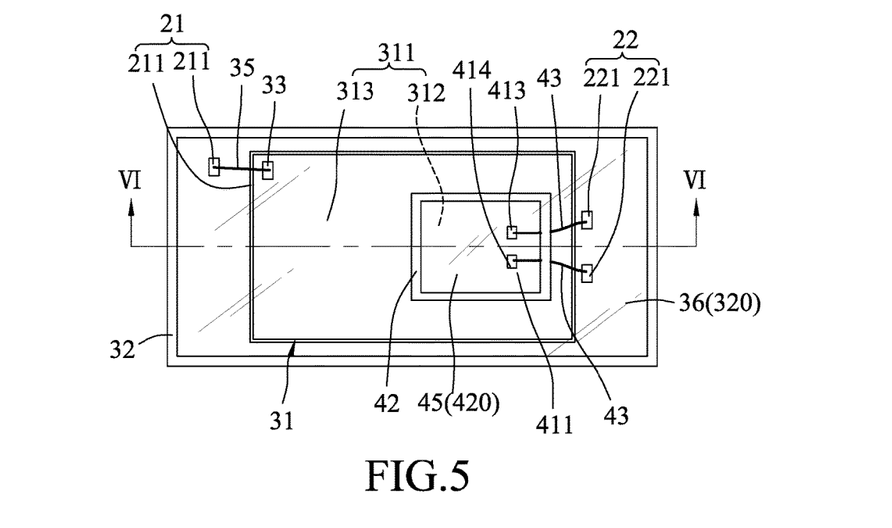
FIG. 5 is a schematic top view of an optical biosensor module according to the second embodiment of this disclosure.
Figure 6:
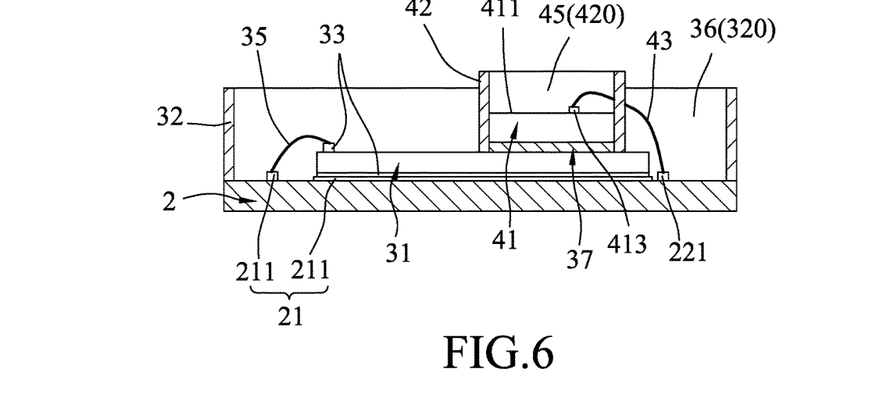
FIG. 6 is a sectional view of the second embodiment taken along line VI-VI of FIG. 5.

Referring to FIGS. 5 and 6, the second embodiment of the optical biosensor module according to this disclosure is generally identical to the first embodiment, and only differs in that the light-receiving unit 3 of the second embodiment only includes the two first electrode pads 33, and the pair of second electrode pads 34 (see FIG. 3) are dispensed herewith. The light-emitting unit 4 is electrically connected to the second circuit 22 through the pair of first conductive wires 43. Specifically, in the second embodiment, the light emitter 41 is directly die-bonded to a non-light transmissive layer 37 of the die mounting region 312 of the light-receiving surface 311. The light emitter 41 and the non-light transmissive layer 37 are directly surrounded by the light emitter blocking wall 42. That is, a periphery of the light emitter 41 and a periphery of the non-light transmissive layer 37 are connected to the light emitter blocking wall 42. The first conductive wires 43 respectively extend from the N-type and P-type contact pads 413, 414 of the light emitter 41 and pass through the light emitter blocking wall 42 to connect directly and respectively with the electrode pads 221 of the second circuit 22 of the circuit board 2. The non-light transmissive layer 37 may be a non-light transmissive die-bonding adhesive, a black adhesive, a metal heat-dissipating layer, or a stack structure of the aforesaid layers.

Figure 7:
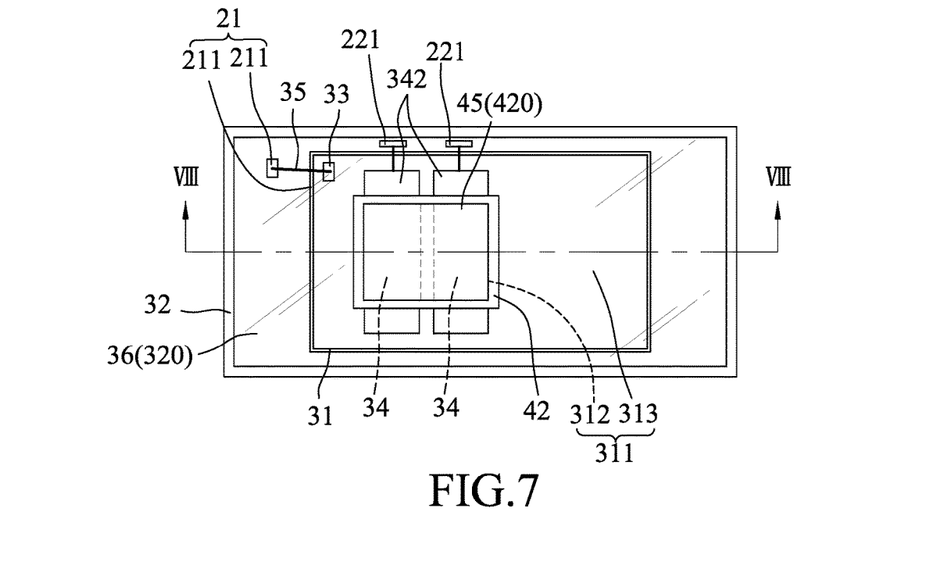
FIG. 7 is a schematic top view of an optical biosensor module according to the third embodiment of this disclosure.
Figure 8:
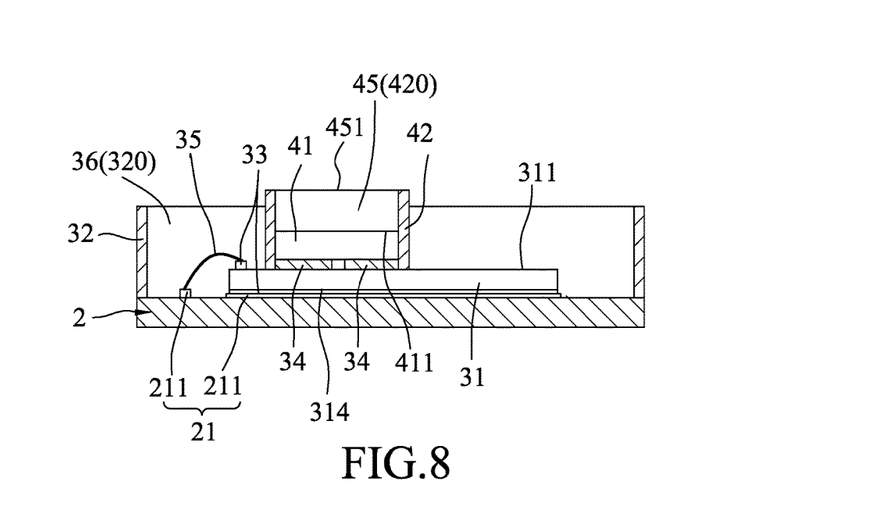
FIG. 8 is a sectional view of the third embodiment taken along line VIII-VIII of FIG. 7.
Figure 9:
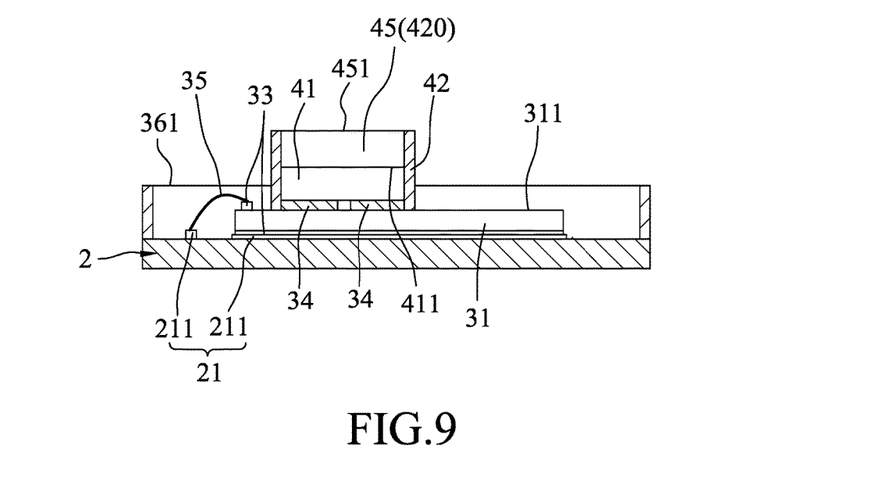
FIG. 9 is a sectional view, illustrating an alternative form of the third embodiment.

Referring to FIGS. 7 and 8, the third embodiment of the optical biosensor module according to this disclosure is generally identical to the first embodiment, and only differs in that the light-emitting unit 4 does not need the first conductive wires 43 shown in FIG. 3 to electrically connect with the pair of second electrode pads 34. Specifically, the pair of second electrode pads 34 are spacedly disposed on the light-receiving surface 311, and the light emitter 41 is flipped-chip mounted to the pair of second electrode pads 34. That is, the N-type and P-type contact pads 413, 414 (see FIG. 2) of the light emitter 41 are disposed on the light emitter 41 opposite to the light-emitting surface 411 and facing the pair of second electrode pads 34, and are connected electrically and respectively to the inner portions 341 (see FIG. 2) of the second electrode pads 34. In this embodiment, the extension portions 342 (see FIG. 2) of the second electrode pads 34 are used to electrically connect with the second circuit (not shown) of the circuit board 2. The connecting method between the extension portions 342 and the second circuit of the circuit board 2 may be as that described in the first embodiment, in which the pair of second conductive wires 44 are used for connecting the extension portions 342 with the second circuit of the circuit board 2; or, a pair of inner connecting circuits (not shown) formed inside the light receiver 31 may be respectively connected to the pair of second electrode pads 34; or, an outer surface of the light receiver 31 is formed with a 3D printed circuit (not shown), since the extension portions 342 extends through the light-receiving surface 311 and a periphery of the light receiver 31 to the bottom surface 314 of the light receiver 31, the extension portions 342 can connect electrically and respectively with the electrode pads 221 of the second circuit of the circuit board 2. An alternative form of this embodiment is shown in FIG. 9, in which the top surface 361 of the second transparent material 36 is lower than the light-emitting surface 411 of the light emitter 41. It should be noted herein that, in this embodiment, the light-emitting unit 4 may be a one-piece structure composed of the light emitter 41, the light emitter blocking wall 42 and the first transparent material 45, for example, a chip scale package (CSP).

Figure 10:
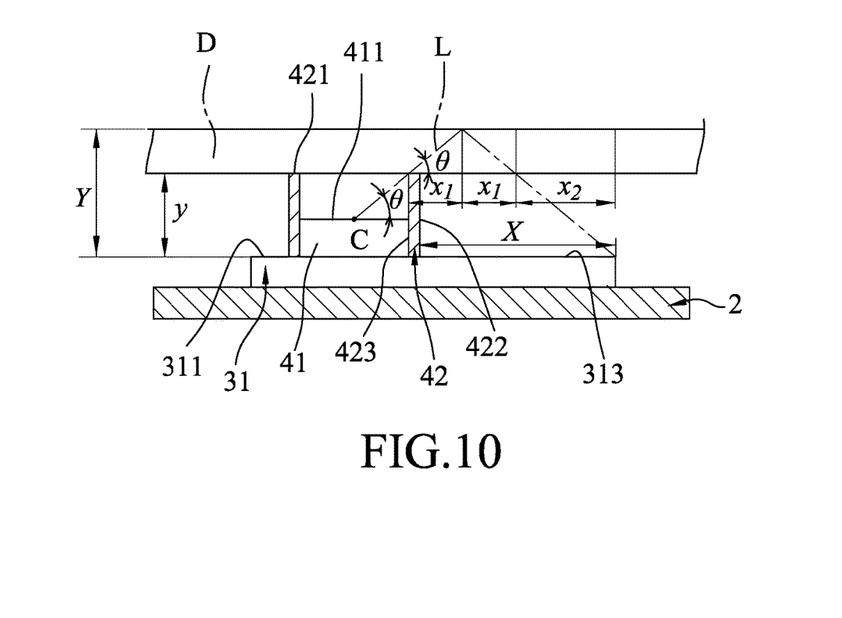
FIG. 10 is a schematic side view, illustrating the position and size relationship between a light-emitting unit and a light receiving unit of the first to third embodiments.

Referring to FIG. 10, the light-emitting unit 4 of the first to third embodiments is disposed on the light-receiving unit 3 such that the light-emitting unit 4 and the light-receiving unit 3 are stacked one above the other on the circuit board 2 so as to prevent the disposition of the light emitter 41 from blocking the optical signal reflected from the skin from entering the light receiver 31. Therefore, in these embodiments, the size of the light receiver 31 is determined based on the size of the light emitter 41, so that the light-receiving region 313 of the light-receiving surface 311 of the light receiver 31 is sufficient enough to receive the optical signal reflected from the skin. Specifically, the light-receiving region 313 of these embodiments has a distance (X) measured from an outer surrounding surface 422 of the light emitter blocking wall 42 to an outer edge of the light receiver 31, the light emitter blocking wall 42 has a height (y) measured from the light-receiving surface 311 to the top side 421 of the light emitter blocking wall 42, a distance (Y) is defined from the light-receiving surface 311 to a dermis layer (D) of the user's skin, and an included angle (θ) is defined by the light-emitting surface 411 and an imaginary line (L) extending from a central point (C) of the light-emitting surface 411 through a junction of an inner surrounding surface 423 and the top side 421 of the light emitter blocking wall 42. From FIG. 10, the distance (X) can be expressed as:

$$X = 2 \times x_1 + x_2 \quad (1)$$

wherein, a constant factor (K) associated with the distance (X) is defined, the light emitter 41 has a viewing angle ($θ_v$), and the relation of $x_1$ and $x_2$ with the distance (Y), the height (y), and the constant factor (K) can be expressed as:

$$X = 2 \times \left( \frac{Y-y}{\tan K} \right) + \frac{y}{\tan K} \quad (2)$$

It should be noted herein that, when the included angle (θ) is greater than 30 degrees, the constant factor (K) is equal to the included angle (θ); and, when the included angle (θ) is smaller than 30 degrees, the constant factor (K) is expressed as K=90−$θ_v$/2. Therefore, through the expression (2), the number of distance (X) the light-receiving region 313 should reserve can be determined, so that the light receiver 31 can effectively receive the optical signal reflected from the user's skin. The light emitter 41 may be placed at a central portion of the light receiver 31, or at a corner of the light receiver 31 to discard a portion of the optical signal, as long as there is at least a size conforming with that of the aforesaid distance (X) exists between the light emitter 41 and the light receiver 31, any position of the light emitter 41 is acceptable.

Figure 11:
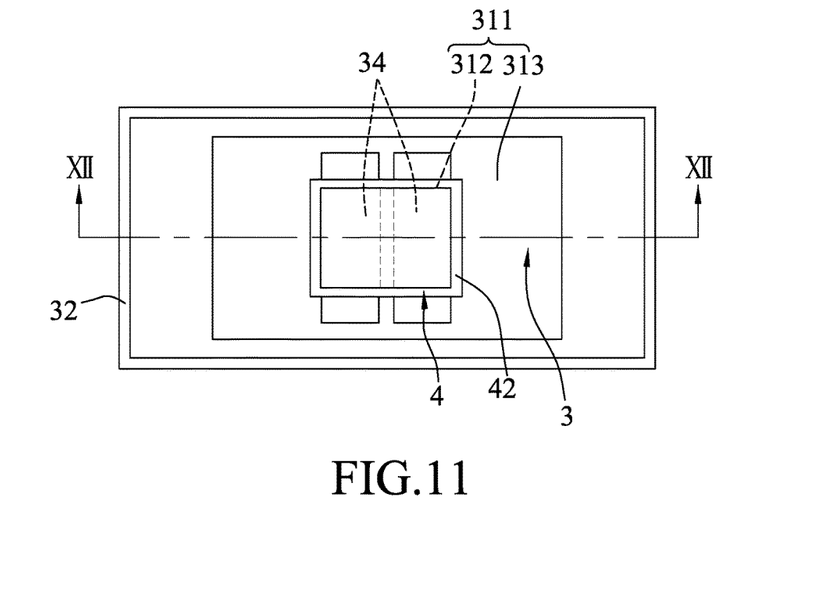
FIG. 11 is a schematic top view of an optical biosensor module according to the fourth embodiment of this disclosure.
Figure 12:
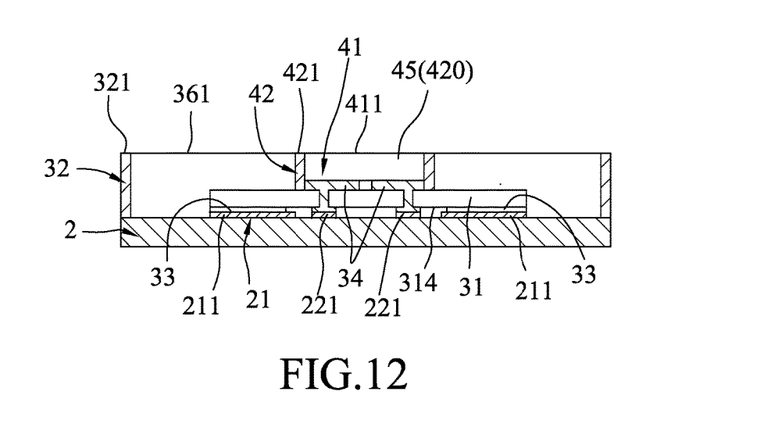
FIG. 12 is a sectional view of the fourth embodiment taken along line XII-XII of FIG. 11.

Referring to FIGS. 11 and 12, the fourth embodiment of the optical biosensor module according to this disclosure is generally identical to the third embodiment, and only differs in that the light-emitting surface 411 of the light emitter 41, the top side 321 of the light receiver blocking wall 32, and the top side 421 of the light emitter blocking wall 42 all have the same height. Specifically, in this embodiment, the bottom surface 314 of the light receiver 31 is formed with the two first electrode pads 33 which are used to connect electrically and respectively the electrode pads 211 of the first circuit 21 of the circuit board 2. Further, a pair of inner connecting circuits formed inside the light receiver 31 are connected electrically and respectively to the pair of second electrode pads 34, the flip chip type light emitter 41 is die-bonded to the pair of second electrode pads 34 through the N-type and P-type contact pads 413, 414 (see FIG. 2) located at a bottom side thereof, and the pair of second electrode pads 34 are connected electrically and respectively to the electrode pads 221 of the second circuit 22 of the circuit board 2. With reference to FIG. 12, in this embodiment, the top surface 361 of the second transparent material 36 is flush with the light-emitting surface 411 of the light emitter 41. Further, the light-emitting unit 4 may be a one-piece structure composed of the light emitter 41 and the light emitter blocking wall 42, for example, a chip scale package (CSP).

Similarly, to prevent the disposition of the light emitter 41 from blocking the optical signal reflected from the skin from entering the light receiver 31, the size of the light receiver 31 can be determined based on the size of the light emitter 41, so that the light-receiving region 313 of the light-receiving surface 311 has the sufficient distance (X) to receive the optical signal reflected from the skin. In the fourth embodiment, since the included angle is smaller than 30 degrees, when calculating the distance (X) using the aforesaid expression (2), the constant factor (K) is expressed as K=90−$θ_v$/2.

To clearly present the connection relationship among the components of the optical biosensor module of the embodiments, a method for making the optical biosensor module is described below.

Figure 13:
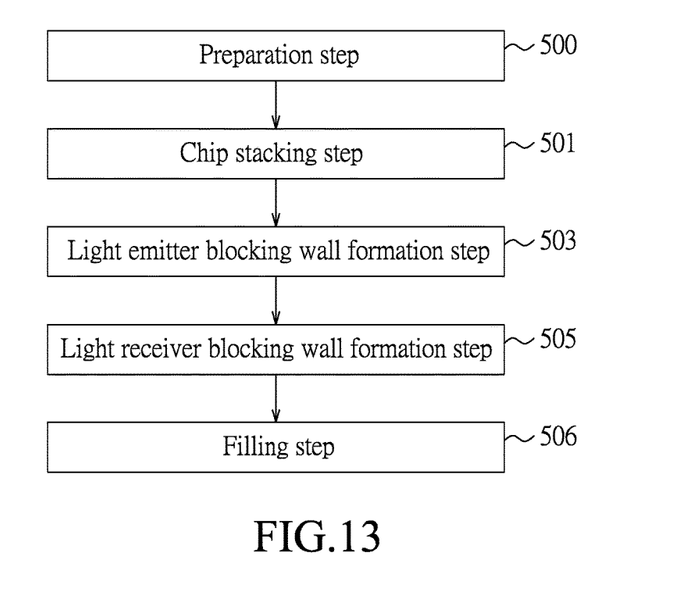
FIG. 13 is a flow diagram, illustrating a method for making an optical biosensor module of this disclosure.

Referring to FIG. 13, a method for making the optical biosensor module according to this disclosure includes a preparation step 500, a chip stacking step 501, a light emitter blocking wall forming step 503, a light receiver blocking wall forming step 505, and a filling (encapsulating) step 506.

In the preparation step 500, the circuit board 2, the light receiver 31 and at least one light emitter 41 are prepared. The circuit board 2 has the mounting surface 20, and the first and second circuits 21, 22. The light receiver 31 has the light-receiving surface 311 with the non-light transmissive die mounting region 312. The light emitter 41 has the light-emitting surface 411.

In the chip stacking step 501, the light receiver 31 is first fixed to the mounting surface 20 of the circuit board 2, after which the light emitter 41 is fixed to the non-light transmissive layer 37 of the die mounting region 312 of the light receiver 31. In this embodiment, the non-light transmissivity of the die mounting region 312 may be achieved through the pair of second electrode pads 34. However, the pair of second electrode pads 34 may be replaced by a non-light transmissive adhesive adhered on the die mounting region 312, or an additional non-light transmissive layer, such as a black adhesive layer or a metal layer, may be disposed on the die mounting region 312.

In the light emitter blocking wall forming step 503, an automatic dispenser, such as a dispensing robot dispenser or an automatic dispenser with pick and place, is used to form the light emitter blocking wall 42 on the light-receiving surface 311 so as to surround the non-light transmissive die mounting region 312, including the light emitter 41, so that light emitted from the light emitter 41 cannot directly transmit to the light-receiving surface 311.

In the light receiver blocking wall forming step 505, a compression molding method or an automatic dispenser with pick and place may be used to form the light receiver blocking wall 32 on the mounting surface 20 of the circuit board 2 so as to surround the light receiver 31.

In the filling step 506, the second transparent material 36 and the first transparent material 45 are poured into the spaces 320, 420 surrounded by the respective light receiver and light emitter blocking walls 32, 42 so as to respectively encapsulate the light receiver 31 and the light emitter 41. If the light emitter 41 is one already having the light emitter blocking wall 42 and the first transparent material 45, in this case, only the second transparent material 36 is poured into the space 320 defined by the light receiver and light emitter blocking walls 32, 42.

Furthermore, based on different forms of the light receiver and the light emitter, different options of electrical connection may be employed in the method. That is, when the light receiver 31 having the first and second electrode pads 33, 34 on the surface thereof is provided, the first electrode pads 33 are connected electrically and respectively to the electrode pads 211 of the first circuit 21 of the circuit board 2, and the second electrode pads 34 are connected electrically and respectively to the electrode pads 221 of the second circuit 22 of the circuit board 2.

Moreover, regarding the selection of suitable light emitter 41 and light receiver 31, the main consideration is that the disposition of the light emitter 41 must not block the optical signal reflected from the skin from entering the light receiver 31. That is, the determination of the size of the light receiver 31 must depend upon the size of the light emitter 41, so that the light-receiving region 313 of the light-receiving surface 311 of the light receiver 31 has the sufficient distance (X) to receive the optical signal reflected from the skin.

With reference to FIG. 10, during the formation of the light emitter blocking wall 42 on the light receiver 31 in the light emitter blocking wall formation step 503, the distance (X) is reserved. That is, the outer surrounding surface 422 of the light emitter blocking wall 42 is spaced apart from the outer edge of the light receiver 31 by the distance (X), the light emitter blocking wall 42 has the height (y), the light-receiving surface 311 is spaced apart from the dermis layer (D) of the user's skin by the distance (Y), and the light-emitting surface 411 cooperates with the imaginary line (L) extending from the central point (C) of the light-emitting surface 411 through the junction of the inner surrounding surface 423 and the top side 421 of the light emitter blocking wall 42 to define the included angle (θ). From FIG. 10, the distance (X) can be expressed as: $X=2\times x_1+x_2$, and the relation thereof with the viewing angle $(\theta_v)$ of the light emitter 41, $x_1$ and $x_2$ can be expressed through the distance (Y), the height (y), and the constant factor (K) as $$X = 2\times\left(\frac{Y-y}{\tan K}\right) + \frac{y}{\tan K}.$$

When the included angle (θ) is greater than 30 degrees, the constant factor (K) is equal to the included angle (θ); and, when the included angle (θ) is smaller than 30 degrees, the constant factor (K) is expressed as $K=90-\theta_v/2$. Thus, the number of the distance (X) to be reserved can be determined, so that the light receiver 31 can effectively receive the optical signal reflected from the user's skin.

Figure 14:
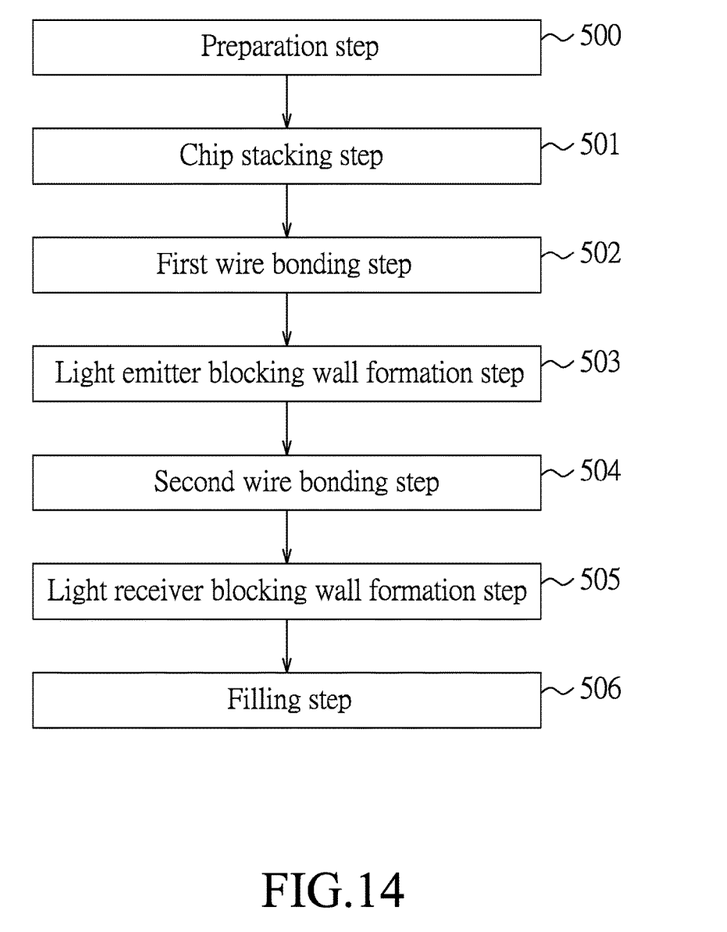
FIG. 14 is a flow diagram, illustrating a method for making the first embodiment.

Additionally, referring to FIG. 14, in combination with FIGS. 2 and 3, the method for making the first embodiment is generally identical to the method shown in FIG. 13, and only differs in that the method of the first embodiment further includes a first wire bonding step 502 after step 501, and a second wire bonding step 504 after step 503. Specifically, in the chip stacking step 501, the first electrode pads 33 on the bottom surface 314 of the light receiver 31 are disposed on the electrode pads 211 of the first circuit 21 located on the mounting surface 20 of the circuit board 2 by a die bonding method, and the light emitter 41 is disposed on the inner portions 341 of the second electrode pads 34 located on the light-receiving surface 311 of the light receiver 31 also by a die bonding method, so that the light emitter 41 is located inside the die mounting region 312 of the light-receiving surface 311, and the light-emitting surface 411 faces away from the light-receiving surface 311. The second electrode pads 34 are non-light transmissive layers of the first embodiment.

In the first wire bonding step 502, the pair of first conductive wires 43 are connected to the N-type and P-type contact pads 413, 414 of the light-emitting surface 411 and the inner portions 341 of the pair of the second electrode pads 34 using a wire bonding method.

In the light emitter blocking wall forming step 503, an automatic dispenser, such as a dispensing robot dispenser or an automatic dispenser with pick and place, is used to form the light emitter blocking wall 42 on the light-receiving surface 311 so as to surround the light emitter 41, the inner portions 341 of the second electrode pads 34 and the first conductive wires 43, so that the extension portions 342 of the second electrode pads 34 are located outside of the light emitter blocking wall 42.

In the second wire bonding step 504, the conductive wire 35 of the light-receiving unit 3 is connected to the first electrode pad 33 located outside of the die mounting region 312 and the first circuit 21 of the circuit board 2 using a wire bonding method, and the pair of second conductive wires 44 of the light-emitting unit 4 are connected to the extension portions 342 of the second electrode pads 34 and the second circuit 22 of the circuit board 2 using also a wire bonding method.

In the light receiver blocking wall forming step 505, a compression molding method or an automatic dispenser with pick and place may be used to form the light receiver blocking wall 32 on the mounting surface 20 of the circuit board 2 so as to surround the light receiver 31.

Figure 15:
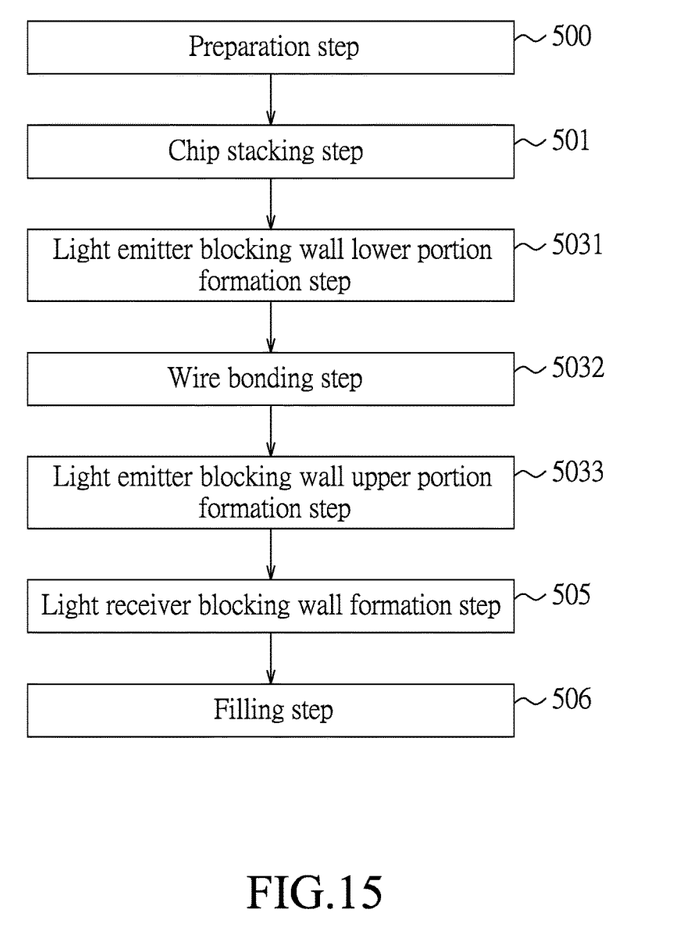
FIG. 15 is a flow diagram, illustrating a method for making the second embodiment.

Referring to FIG. 15, in combination with FIGS. 5 and 6, the method of the second embodiment is generally identical to the method shown in FIG. 13, and differs in that the light emitter blocking wall forming step 503 in FIG. 13 is divided into a light emitter blocking wall lower portion formation step 5031 and a light emitter blocking wall upper portion formation step 5033, and the method of the second embodiment further includes a wire bonding step 5032 between the light emitter blocking wall lower and upper portion formation steps 5031, 5033.

Concretely speaking, after the chip stacking step 501, the light emitter blocking wall lower portion formation step 5031 is performed, in which a lower portion of the light emitter blocking wall 42 is formed on the light-receiving surface 311 and surrounds the light emitter 41 using an automatic dispenser.

In the wire bonding step 5032, the conductive wire 35 of the light-receiving unit 3 is connected between the first electrode pad 33 located outside of the die mounting region 312 of the light-receiving surface 311 and one of the electrode pads 211 of the first circuit 21 using a wire bonding method, and the pair of first conductive wires 43 of the light-emitting unit 4 are connected to the N-type and P-type contact pads 413, 414 of the light-emitting surface 411 and the second circuit 22 of the circuit board 2 using also a wire bonding method such that the pair of first conductive wires 43 cross over the preformed lower portion of the light emitter blocking wall 42.

In the light emitter blocking wall upper portion formation step 5033, an upper portion of the light emitter blocking wall 42 is formed on top of the lower portion thereof using the automatic dispenser, thereby obtaining the complete light emitter blocking wall 42.

With reference to FIGS. 7 and 8, the method of the third embodiment is generally identical to the method of the first embodiment shown in FIG. 14. However, there is no first wire bonding step 502 in the third embodiment. Further, in the chip stacking step 501 of this embodiment, the light emitter 41 is directly connected to the pair of second electrode pads 34 of the light receiver 31 using a flip-chip method. Since the electrical connection between the light emitter 41 and the circuit board 2 has been described in the foregoing, it will not be repeated herein for the sake of brevity. Moreover, in the second wire bonding step 504 of this embodiment, only the conductive wire 35 of the light-receiving unit 3 is connected between the first electrode pad 33 located outside of the die mounting region 312 of the light-receiving surface 311 and one of the electrode pads 211 of the first circuit 21 of the circuit board 2 using a wire bonding method.

Referring to FIGS. 11 and 12, the method of the fourth embodiment is generally identical to the method of the third embodiment, and only differs in that there is no second wire bonding step 504 in the fourth embodiment. Specifically, in the chip stacking step 501 of this embodiment, the first electrode pads 33 on the bottom surface 314 of the light receiver 31 are connected directly, electrically and respectively to the electrode pads 211 of the first circuit 21 of the circuit board 2.

From the detailed description of the foregoing paragraphs, it is apparent that the light-emitting unit 4 of each embodiment of this disclosure is disposed on the light-receiving surface 311 of the light receiver 31 such that the light emitter 41 and the light receiver 31 are stacked one above the other on the circuit board 2, not only can the two-dimensional space of each embodiment be reduced to achieve the effect of reducing the sizes of the components and the size of the wearable device, but also the light emitter 41 facing the user's skin can be closer to the user, thereby shortening the optical path of the incident light and reducing the loss of light to achieve a power saving effect.

Furthermore, in each of the first to third embodiments, because the top side 421 of the light emitter blocking wall 42 is made higher than the top side 321 of the light receiver blocking wall 32 and the light-emitting surface 411 of the light emitter 41 so that the top side 421 of the light emitter blocking wall 42 is highest with respect to the light receiver 31 and the light emitter 41, the incident light emitted from the light emitter 41 will not enter directly and laterally the light-receiving surface 311 of the light receiver 31 so as to interfere with the optical signal received by the light receiver 31. Also, in each of the first to third embodiments, there is no light transmissivity between the light receiver 31 and the light emitter 41 so as to prevent the incident light emitted from the light emitter 41 to directly enter the light-receiving surface 311 of the light receiver 31 and to reduce interference with the optical signal received by the light receiver 31.

Moreover, in each of the embodiments, the second transparent material 36 contains dye for filtering the unnecessary noise, and the top surface 361 of the second transparent material 36 and the top surface 451 of the first transparent material 45 having concave shapes can increase the divergent angle of the incident light emitting from the light emitter 41 and leaving the first transparent material 45 to enhance the light receiving effect of the light receiver 31.

In sum, the light-emitting unit 4 and the light-receiving unit 3 of the optical biosensor module of this disclosure are stacked one above the other on the circuit board 2 so as to reduce the sizes of the components thereof, so that the size of the wearable device can also be reduced, and the optical path of the light emitter 41 with the user can be shortened to reduce loss of light and save electricity. Further, the top surface 451 of the first transparent material 45 is made higher than the top surface 361 of the second transparent material 36, the top side 421 of the light emitter blocking wall 42 is made higher than the top side 321 of the light receiver blocking wall 32, and no light transmissivity between the light receiver 31 and the light emitter 41, so that the incident light emitted from the light emitter 41 can be prevented from traveling sideways or toward the light-receiving surface 311 to reduce interference with the optical signal received by the light receiver 31. Moreover, the second transparent materials 36 containing dye can filter the unnecessary noise, and the concave top surfaces 361, 451 of the second and first transparent materials 36, 45 can increase the divergent angle of the incident light emitting from the light emitter 41 to enhance the light receiving effect of the light receiver 31. Therefore, the objects of this disclosure can indeed be achieved.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the most practical embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An optical biosensor module comprising:
a circuit board including a mounting surface, a first circuit and a second circuit;
a light-receiving unit disposed on said mounting surface, said light-receiving unit including a light receiver electrically connected to said first circuit and having a light-receiving surface that faces away from said mounting surface, and a light receiver blocking wall surrounding said light receiver; and
a light-emitting unit disposed on said light-receiving surface and including a light emitter electrically connected to said second circuit and having a light-emitting surface that faces away from said light-receiving surface, and a light emitter blocking wall surrounding said light emitter;
wherein an opaque interface exists between said light receiver and said light emitter; and
wherein a top side of said light emitter blocking wall is equal to or higher than said light-emitting surface.

2. The optical biosensor module as claimed in claim 1, wherein said light-receiving surface includes a die mounting region located inside said light emitter blocking wall, said light receiver includes a pair of first electrode pads electrically connected to said first circuit, and said light emitter includes an N-type contact pad and a P-type contact pad, said light emitter being electrically connected to said second circuit through said N-type and P-type contact pads.

3. The optical biosensor module as claimed in claim 2, wherein said light receiver further includes a pair of second electrode pads disposed spaced apart on said light-receiving surface, each of said second electrode pads having an inner portion located inside said die mounting region, and an extension portion extending from said inner portion to the outside of said die mounting region, said N-type and P-type contact pads being connected electrically and respectively to said inner portions of said second electrode pads, said extension portions of said second electrode pads being electrically connected to said second circuit.

4. The optical biosensor module as claimed in claim 1, wherein said top side of said light emitter blocking wall is equal to or higher than a top side of said light receiver blocking wall.

5. The optical biosensor module as claimed in claim 1, wherein:
said light-receiving surface includes a die mounting region located inside said light emitter blocking wall and a light-receiving region surrounding said die mounting region, said light-receiving region having a distance (X) measured from an outer surrounding surface of said light emitter blocking wall to an outer edge of said light receiver;
said light emitter blocking wall has a height (y) measured from said light-receiving surface to said top side of said light emitter blocking wall;
a distance (Y) is defined from said light-receiving surface to a dermis layer (D) of a user's skin;
a constant factor (K) associated with the distance (X) is defined;
said light emitter has a viewing angle ($\theta_v$);
an included angle ($\theta$) is defined by said light-emitting surface and an imaginary line (L) extending from a central point (C) of said light-emitting surface through a junction of an inner surrounding surface and said top side of said light emitter blocking wall, said distance (X) being expressed as:

$$X = 2 \times \left(\frac{Y-y}{\tan K}\right) + \frac{y}{\tan K}$$

when said included angle ($\theta$) is greater than 30 degrees, the constant factor (K) is equal to said included angle ($\theta$); and
when said included angle ($\theta$) is equal to or smaller than 30 degrees, the constant factor (K) is expressed as $K = 90 - \theta_v/2$.

6. The optical biosensor module as claimed in claim 1, wherein said light-emitting unit further includes a first transparent material filled into a space surrounded by said light emitter blocking wall to encapsulate said light emitter.

7. The optical biosensor module as claimed in claim 6, wherein said light-receiving unit further includes a second transparent material filled into a space cooperatively defined by said light receiver blocking wall and said light emitter blocking wall to encapsulate said light receiver and to cover said mounting surface.

8. The optical biosensor module as claimed in claim 7, wherein said first transparent material has a top surface concave downwardly from said top side of said light emitter blocking wall toward said light emitter, and said second transparent material has a top surface concave downwardly from said top side of said light receiver blocking wall toward said light receiver.

9. The optical biosensor module d as claimed in claim 1, wherein said light receiver blocking wall and said light emitter blocking wall are respectively made of an opaque material that can block an incident light emitted from said light emitter from penetrating therethrough.

10. The optical biosensor module d as claimed in claim 1, wherein a height measured from said mounting surface to said top side of said light emitter blocking wall is higher than a height measured from said mounting surface to a top side of said light receiver blocking wall by at least 3 percent (3%) and does not exceed twice the height measured from said mounting surface to said top side of said light receiver blocking wall.

11. A method for making an optical biosensor module comprising:
a preparation step, in which a circuit board having a mounting surface, a light receiver having a light-receiving surface, and a light emitter having a light-emitting surface are prepared;
a chip stacking step, in which the light receiver is disposed on the mounting surface, and the light emitter is disposed on a non-light transmissive layer of a die mounting region of the light-receiving surface;
a light emitter blocking wall forming step, in which a light emitter blocking wall is formed on the light-receiving surface and surrounds the die mounting region and the light emitter; and a light receiver blocking wall forming step, in which a light receiving blocking wall is formed on the mounting surface and surrounds the light receiver and the light emitter blocking wall.

12. The method as claimed in of claim 11, further comprising a filling step, in which a second transparent material is poured into a space cooperatively defined by the light receiver blocking wall and the light emitter blocking wall to encapsulate the light receiver.

13. The method as claimed in of claim 12, wherein:
the light-receiving surface further includes a light-receiving region surrounding the die mounting region, the light-receiving region having a distance (X) measured from an outer surrounding surface of the light emitter blocking wall to an outer edge of the light receiver;
the light emitter blocking wall has a height (y) measured from the light-receiving surface to the top side of the light emitter blocking wall;
a distance (Y) is defined from the light-receiving surface to a dermis layer (D) of a user's skin;
a constant factor (K) associated with the distance (X) is defined;
the light emitter has a viewing angle ($\theta_v$);
an included angle ($\theta$) is defined by the light-emitting surface and an imaginary line (L) extending from a central point (C) of the light-emitting surface through a junction of an inner surrounding surface and the top side of the light emitter blocking wall, the distance (X) being expressed as:

$$X = 2 \times \left(\frac{Y-y}{\tan K}\right) + \frac{y}{\tan K}$$

when the included angle ($\theta$) is greater than 30 degrees, the constant factor (K) is equal to the included angle ($\theta$); and
when the included angle ($\theta$) is smaller than 30 degrees, the constant factor (K) is expressed as K=90−$\theta_v$/2.

* * * * *